(12) United States Patent
Woolley

(10) Patent No.: US 6,575,913 B1
(45) Date of Patent: Jun. 10, 2003

(54) RELATING TO SPHYGMOMETERS

(75) Inventor: Jack Woolley, College Cross (GB)

(73) Assignee: A.C. Cossor & Son (Surgical) Limited, Greater London (GB)

( * ) Notice: Subject to any disclaimer, the term of this patent is extended or adjusted under 35 U.S.C. 154(b) by 0 days.

(21) Appl. No.: 09/889,835

(22) PCT Filed: Jan. 28, 2000

(86) PCT No.: PCT/GB00/00264

§ 371 (c)(1),
(2), (4) Date: Jul. 23, 2001

(87) PCT Pub. No.: WO00/44277

PCT Pub. Date: Aug. 3, 2000

(30) Foreign Application Priority Data

| Feb. 1, 1999 | (GB) | ............................................... 9902191 |
| Feb. 1, 1999 | (GB) | ............................................... 9902192 |
| Feb. 1, 1999 | (GB) | ............................................... 9902193 |

(51) Int. Cl.⁷ .................................................. A61B 5/02
(52) U.S. Cl. ..................................................... 600/490
(58) Field of Search ............................ 24/21; 600/490, 600/491, 492, 499, 485

(56) References Cited

U.S. PATENT DOCUMENTS 4,206,765 A * 6/1980 Huber ......................... 600/490
4,211,289 A * 7/1980 Klein .......................... 172/686
4,901,732 A * 2/1990 Williams ..................... 600/499

FOREIGN PATENT DOCUMENTS

DE 3426183 A1 * 2/1986 ............. A61B/5/02
DE 3533513 A1 * 4/1987 ............. A61B/5/02

* cited by examiner

*Primary Examiner*—Max F. Hindenburg
*Assistant Examiner*—Jonathan Foreman
(74) *Attorney, Agent, or Firm*—Martin Fleit; Paul D. Bianco; Fleit, Kain, Gibbons, Gutman & Bongini PL

(57) ABSTRACT

A cuff member for a sphygmomanometer that has a manually rotatable spindle mounted in a housing. One end of an inflatable cuff is attached to and wound spirally on the spindle. The spiral-wound portion of the cuff in use remaining at least partially inflatable but provides the effect of a constriction at a position along its length dependent on the extent of the spiral wound portion. The inflatable cuff extends through an opening in the housing. An end unit is attached to the other end of the inflatable cuff. A releasable fastening member fastens the end unit to the housing. A desired effective length of cuff is withdrawn from the housing via the opening to extend in a loop around the upper arm of a patient. A ratchet cooperates with the spindle to allow withdrawal of the cuff from the housing when the spindle is manually rotated in one direction and to restrain withdrawal of the cuff from the housing for rotation of the spindle in the opposite direction.

11 Claims, 11 Drawing Sheets

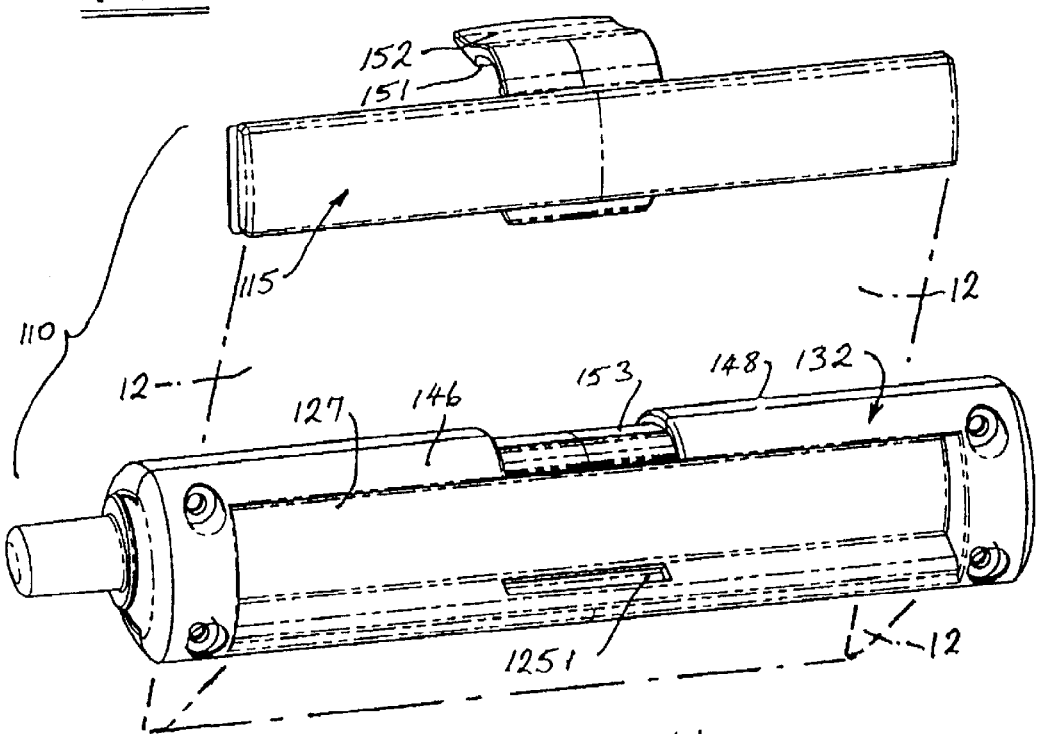
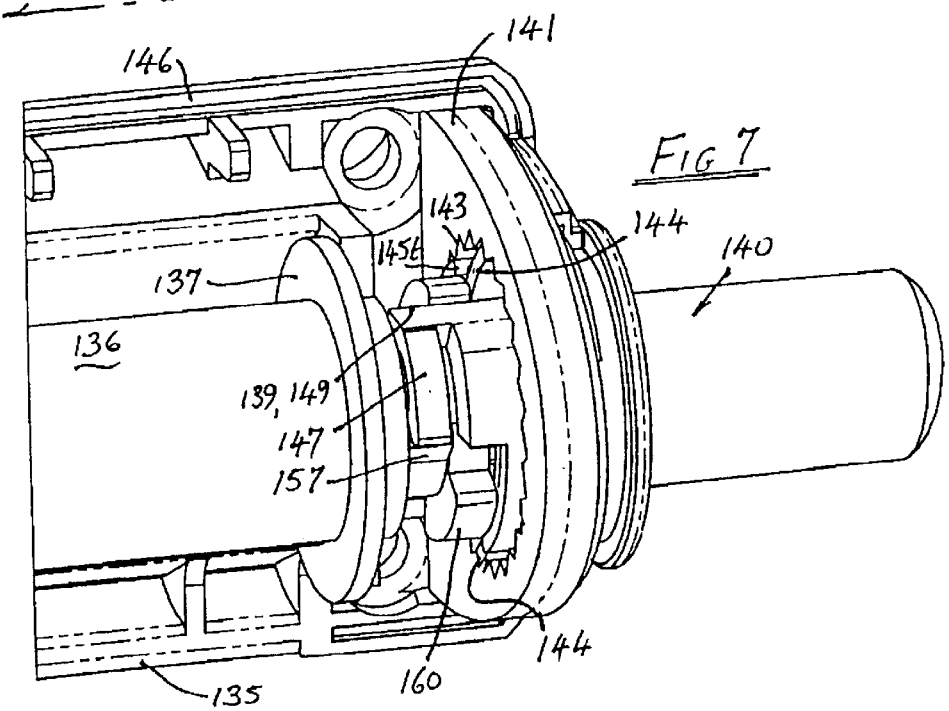

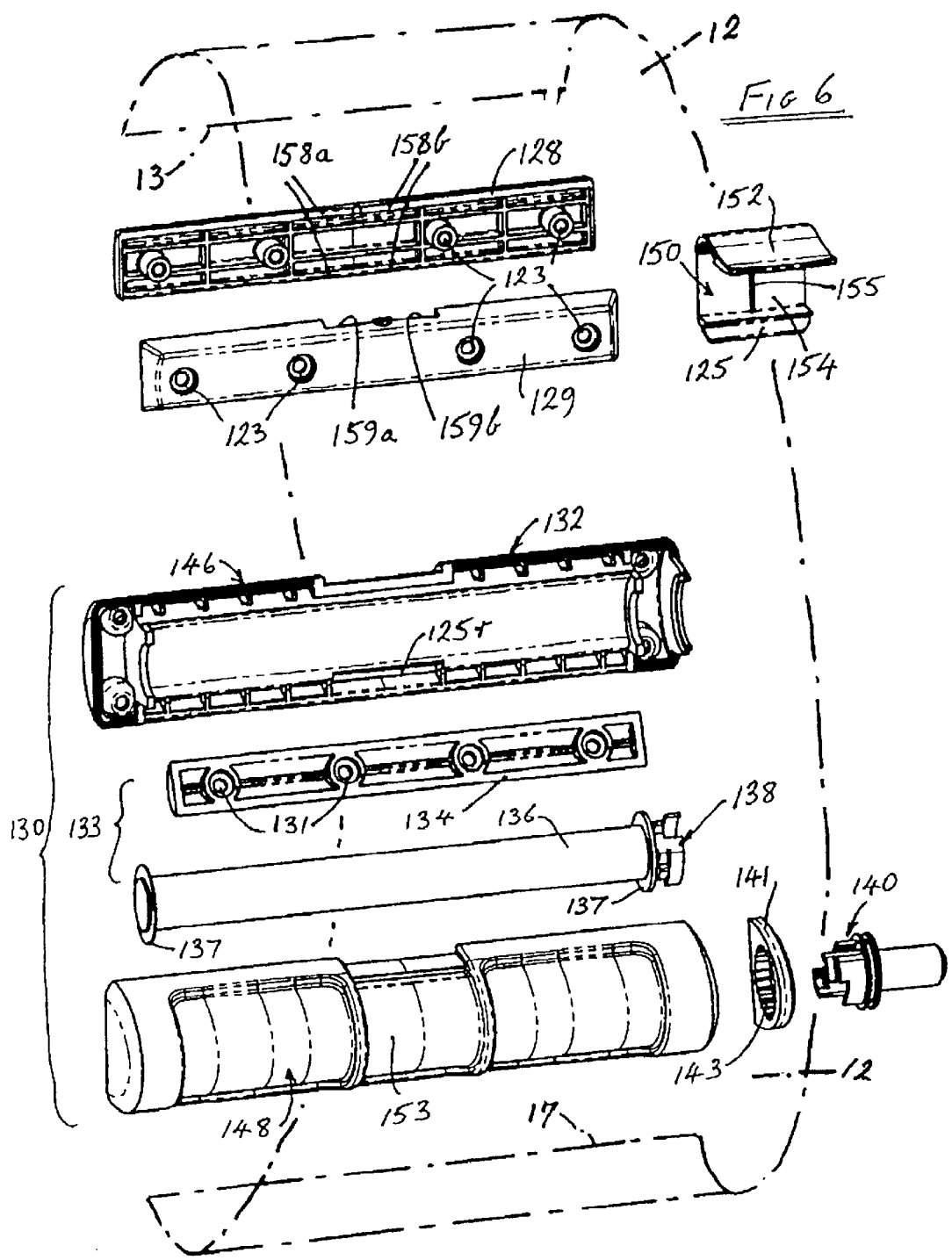

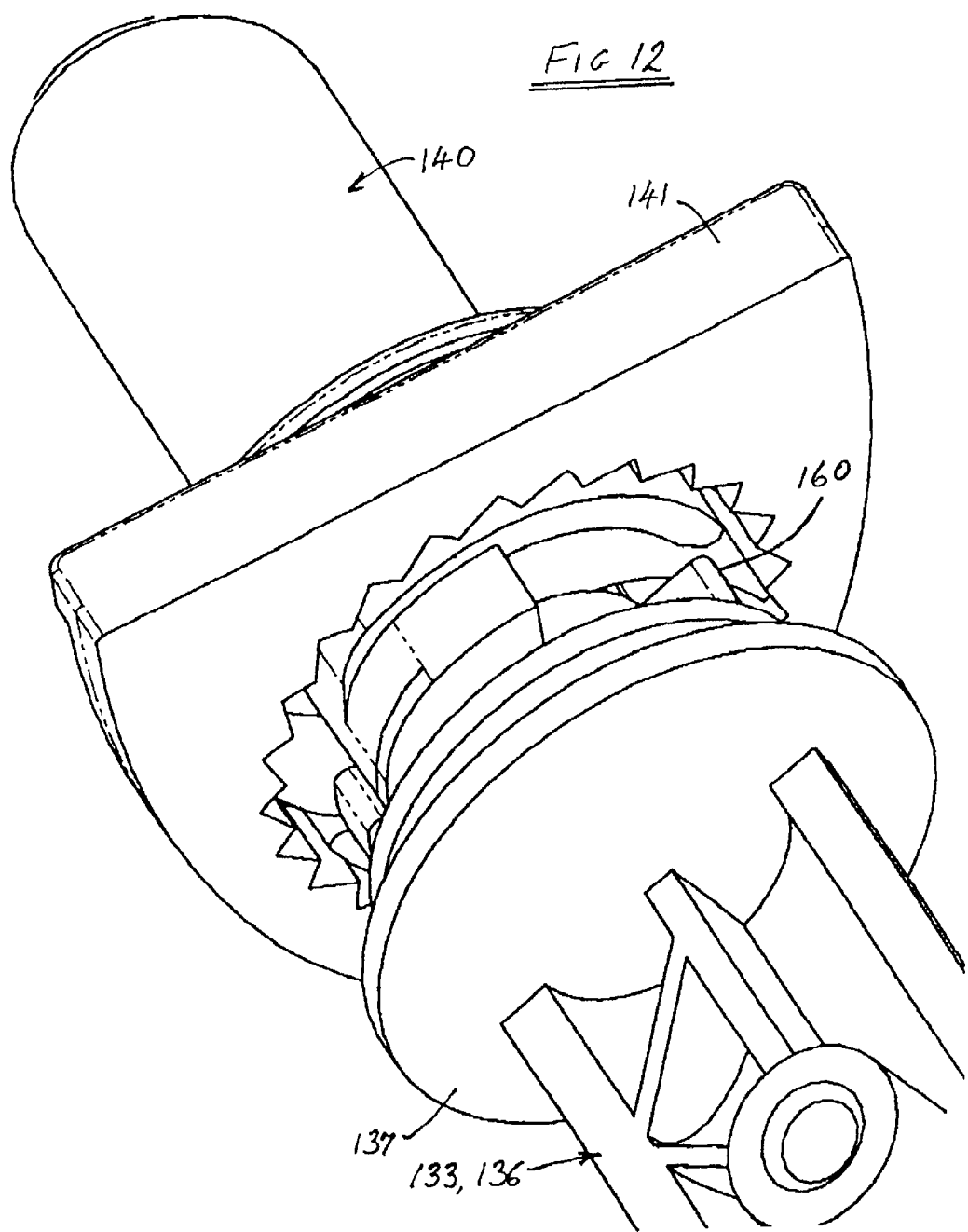

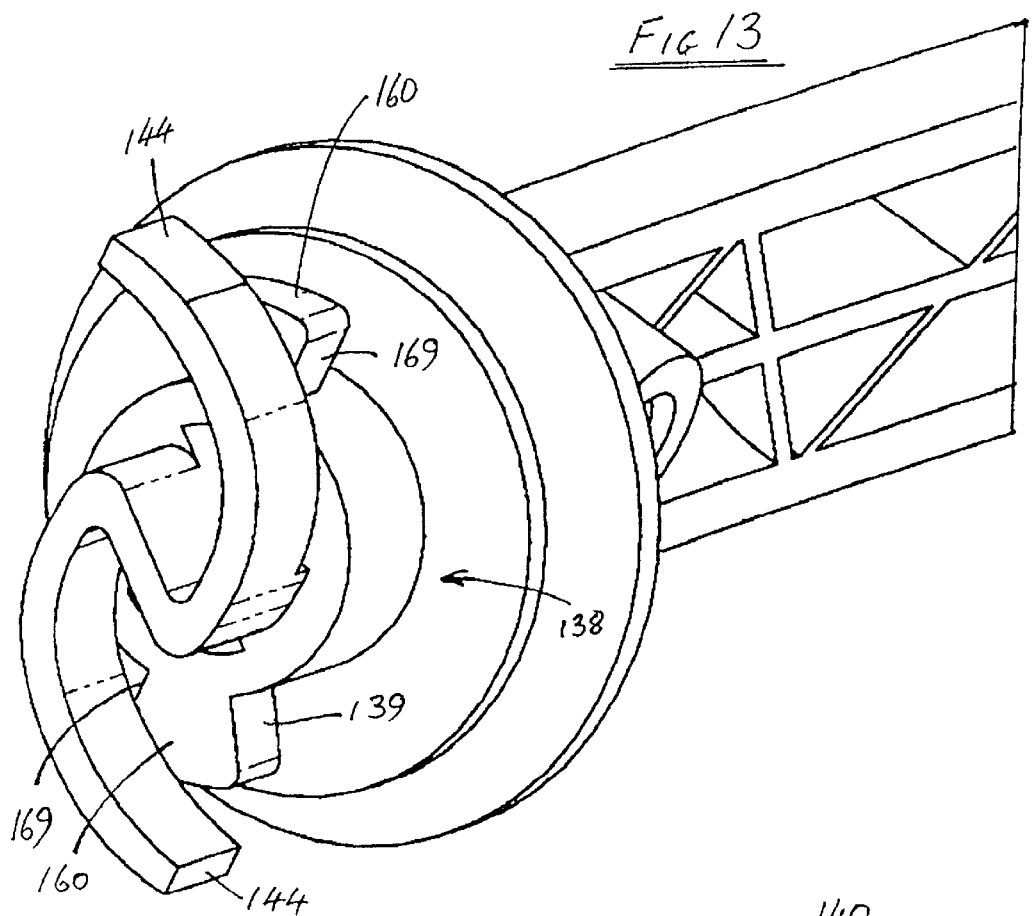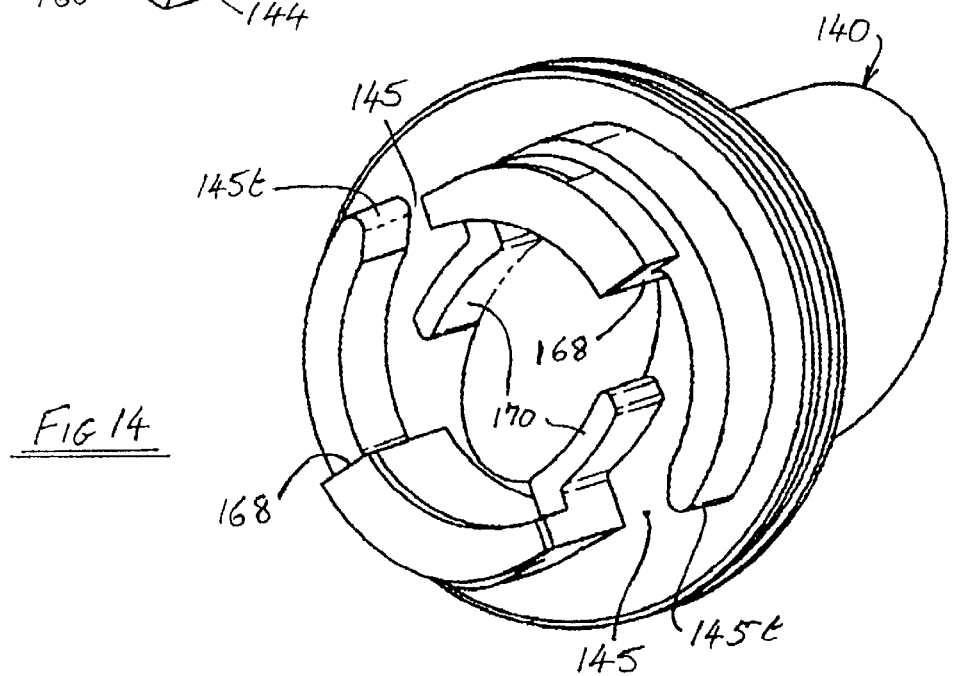

RELATING TO SPHYGMOMETERS

TECHNICAL FIELD

This invention relates to sphygmomanometers and other devices.

BACKGROUND ART

It is a well-known medical and veterinary diagnostic procedure to use a sphygmomanometer to obtain a measure of the hydrostatic pressure under which blood exists in the arteries and veins of human beings and animals. The most common sphygmomanometer comprises (a) a bag or bladder forming or contained in a cuff, the bladder being inflatable with air by a hand bulb communicating with the bladder via a one-way relief or regulator valve, and (b) a pressure guage or like pressure measuring instrument that communicates with the air inside the bag and provides a measure of the pressure (and that is generally expressed in mm of mercury).

In the auscultation method for obtaining a measure of blood pressure, the bladder or bag is wrapped around the subject's arm (usually the left arm) above the elbow in a position appropriate to shut off blood flow in the brachial artery—the principal artery of the upper arm—when the bag is inflated. Utilising the hand bulb, air is pumped into the bag until the subject's pulse in the brachial artery disappears. This is noted by the clinician (i.e. doctor, nurse or other operator) listening via a stethoscope placed over the brachial artery in the vicinity of, (e.g. just below) the elbow, for the faint tapping sounds corresponding to the heartbeat. After effective closure of the brachial artery, the air pressure within the bladder is then allowed to decrease slowly via the one-way relief valve whilst the clinician listens, via the stethoscope, for the first onset of the faint tapping sounds corresponding to the heartbeat to re-appear. The reading of the guage at this moment gives the systolic blood pressure, i.e. the pressure necessary to suppress the maximum pressure of blood in the artery. The air pressure within the bladder is then further decreased slowly, via the one-way relief valve, whilst the pulse beat is monitored. As the air pressure compressing the artery is diminished, the sounds become progressively louder and eventually change in quality from loud to soft before they ultimately disappear. This corresponds to the pressure at which the maximum pulse wave is (again) obtained and marks the diastolic blood pressure, i.e. the pressure when the heart is in diastole with arterial pressure at its minimum.

Recent studies, notably by the British Hypertension Society and Professor O'Brien of Beaumont Hospital, Dublin (Ireland), suggest that the accuracy of the results of blood pressure measurement can be assured (a) if there is no overlap of the ends of the inflatable bladder and (b) if the inflated bladder extends around as near as possible to 100% of the subject's arm, preferably at least 80% of the circumference of the subject's arm.

It will be appreciated that achieving such desiderata is extremely difficult in practice due to the considerable arm size variations between different people. Further difficulties arise due to the varying degrees of taper of the upper arm from one person to another.

One previously-proposed solution is to provide a range of differently sized cuffs and select one to fit the patient whose blood pressure is to be measured. This is time consuming and in a clinic or hospital, requires increased stock levels of the differently-sized cuffs.

Another previously-proposed solution is to provide a single external cuff which houses therein three separate bladders of different length (and width) dimension, only the bladder of the requisite size being inflated in use. This cuff is a multi-layered structure prone to leakage or failure and is also an expensive item.

Another, and not necessarily related, field concerns ratchet mechanisms and in particular to ratchet mechanisms involving relative arcuate movement between the ratcheting parts.

It is a well-known to provide a rotary ratchet mechanism in which the ratchet and pawl may be disengaged by depressing a button in a generally radial direction to deflect the pawl out of enagagement of the ratchet teeth. Where the rotary ratchet mechanism has no spring or like resilient means to effect counter-rotation when the ratchet and pawl are disengaged, the disengagement procedure is generally an inconvenient two-handed operation requiring one hand to effect rotation or counter-rotation of the rotary member of the ratchet mechanism and the other hand to effect depression of the disengagement button.

It is therefore considered desirable to overcome or at least minimise one or more of the aforesaid and/or other difficulties.

SUMMARY OF THE INVENTION

According to a first aspect of this invention there is provided, for a sphygmomanometer, cuff means comprising an inflatable cuff having a length susceptible to inflation, and constriction means to constrict the cuff at different positions along it thereby to vary the said length from a maximum to an effective length less than the maximum.

According to a second aspect of this invention there is provided, for a sphygmomanometer, cuff means comprising an inflatable cuff having a length susceptible to inflation, and constriction means relatively moveable with respect to the cuff and thereby to constrict the cuff at different positions along it whereby the said length can be varied from a maximum to a desired effective length less than the maximum.

Advantageously the constriction means is operable to vary said length continuously such as to select or pre-set any desired effective length for the cuff (preferably in the range of about 20% to 100% of the maximum length).

Preferably the cuff means comprises a housing, a spindle rotatable therein to which one end of the inflatable cuff is attached, an opening in the housing through which the inflatable cuff may extend, and an end unit to which the other end of the inflatable cuff is attached, said end unit being in use releasably fastened to the housing such that a desired effective length of cuff can be withdrawn from the housing via said opening to extend in a loop around the upper arm of a patient.

The remaining portion of the cuff wound around the spindle within the housing is constricted against inflation by such winding and/or by its engagement of the opening. In this regard it will be appreciated that, being a pressure application device, small differences in the effective length of the cuff (providing the external loop) are unlikely to have a material significance. It is this loop which in use extends around the upper arm of the subject whose blood pressure is to be taken (i.e. measured).

In one preferred embodiment the opening is provided by a slot formed between two co-operating parts of the housing.

Advantageously the end unit and the housing are provided with mutually co-operable snap-fastening attachment means.

Preferably, releasable fastening means—to fasten said end unit releasably to the housing—is attached to one or other of the end unit and housing in a manner permitting their relative twisting. This permits the portion of the cuff that extends between the end unit and the housing—and which in use forms a loop around the patient's upper arm—to accommodate the tapering nature of the patient's upper arm.

Preferably the degree of permitted angular twisting is in the range 5° to 15°.

According to a third aspect of this invention there is provided, for a sphygmomanometer, cuff means comprising an inflatable cuff having a length susceptible to inflation, and means permitting the cuff, in use, to adopt a frusto-conical form to accomodate the taper of a subject's limb, e.g. the upper arm of a human patient.

According to a fourth aspect of this invention there is, provided, for a sphygmomanometer, cuff means comprising an inflatable cuff having a length susceptible to inflation, and fastening means comprising first and second mutually interengageable parts spaced apart longitudinally of the cuff, one of said parts being attached to the cuff by means permitting the fastened cuff, in use, to adopt a frusto-conical form.

By permitting the fastened cuff, in use, to adopt a frusto-conical form, varying degrees of taper of the upper arm can be accomodated thus allowing cuff use for a wide range of people with different arm sizes and tapers.

Preferably the cuff means comprises a ratchet mechanism to restrain withdrawal of the cuff from the housing, and release means operable to permit such withdrawal.

Advantageously said releasable ratchet mechanism is one-hand operable and comprises a rotatable input member (e.g. a knob unit) and a rotatable output member (e.g. a spindle, preferably coaxial with the rotatable input member), rotation of the input member in a first direction effecting rotation of the output member in that direction but preventing rotation of the output member in a second, opposite direction, and rotation of the input member in the opposite second direction permitting rotation of the output member in that second direction.

Preferably this is achieved by providing first and second mutually engageable ratchet means that, when the input member is rotated in said first direction are in mutual cooperative engagement to prevent said rotation of the output member in the second direction, and that are disengaged when the input member is rotated in the said opposite, second direction—to permit said rotation of the output member in the second direction.

According to a fifth aspect of this invention there is provided a releasable ratchet mechanism that is one-hand operable and comprises a rotatable input member, a rotatable output member, and mutually engageable ratchet means effecting selectively disengageable coupling between the said input and output members such that rotation of the input member in a first direction effects rotation of the output member in that direction but prevents rotation of the output member in a second, opposite direction, and such that rotation of the input member in the opposite second direction permits rotation of the output member in that second direction.

Preferably the ratchet mechanism comprises first and second mutually engageable ratchet means that, when the input member is rotated in said first direction, are in mutual co-operative engagement to prevent said rotation of the output member in the second direction and that are disengaged when the input member is rotated in the said opposite, second direction—to permit said rotation of the output member in the second direction.

Advantageously, the mechanism comprises a pawl fast with one member (preferably the output member) for extension through a slot in the other member (preferably the input member) and to engage an arcuate array of fixed ratchet teeth, one of the bounding edges of said slot deflecting the pawl inwardly when the other member is rotated in said second direction.

BRIEF DESCRIPTION OF THE DRAWINGS

By way of example, embodiments of this invention will now be described with reference to the accompanying drawings of which:

FIG. 5 is a diagrammatic perspective view of a second sphygmomanometer embodying one or more aspects of the present invention, FIG. 6 is an exploded view of parts of the sphygmomanometer of FIG. 5, FIG. 7 is an enlarged view showing parts of a ratchet device shown in FIG. 6, FIG. 12 is a perspective view, corresponding generally to FIG. 9, of interengaged ratchet device parts of a third sphygmomanometer embodying one or more aspects of the present invention—and being a modification of the embodiment shown in FIGS. 7 to 11, FIG. 13 is a perspective view of the end of a spindle part that is shown in FIG. 12, FIG. 14 is a perspective view of the end of a knob unit that is shown in FIG. 12.

DETAILED DESCRIPTION OF EXAMPLE(S) OF THE INVENTION

Figure 1:
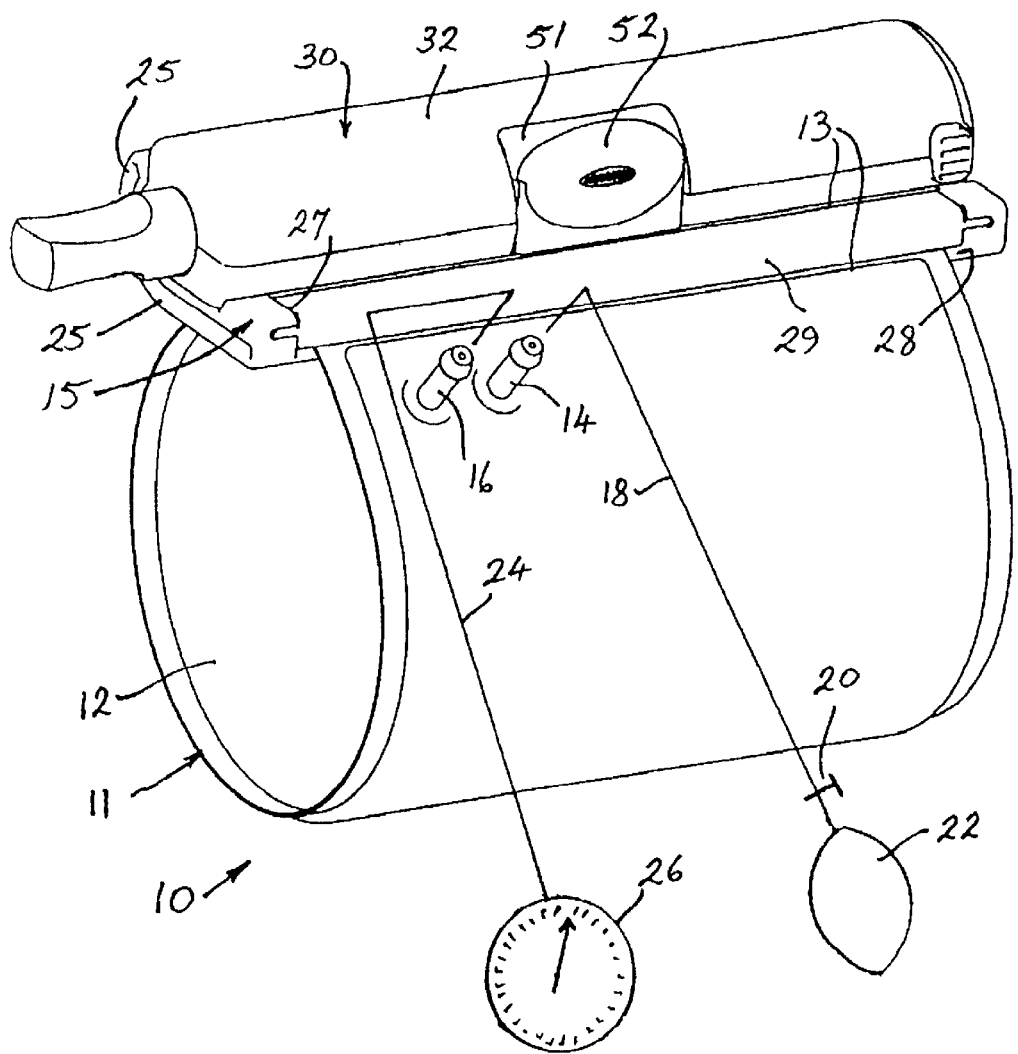
FIG. 1 is a diagrammatic perspective view (from the front and one side) of a sphygmomanometer embodying one or more aspects of the present invention.
Figure 2:
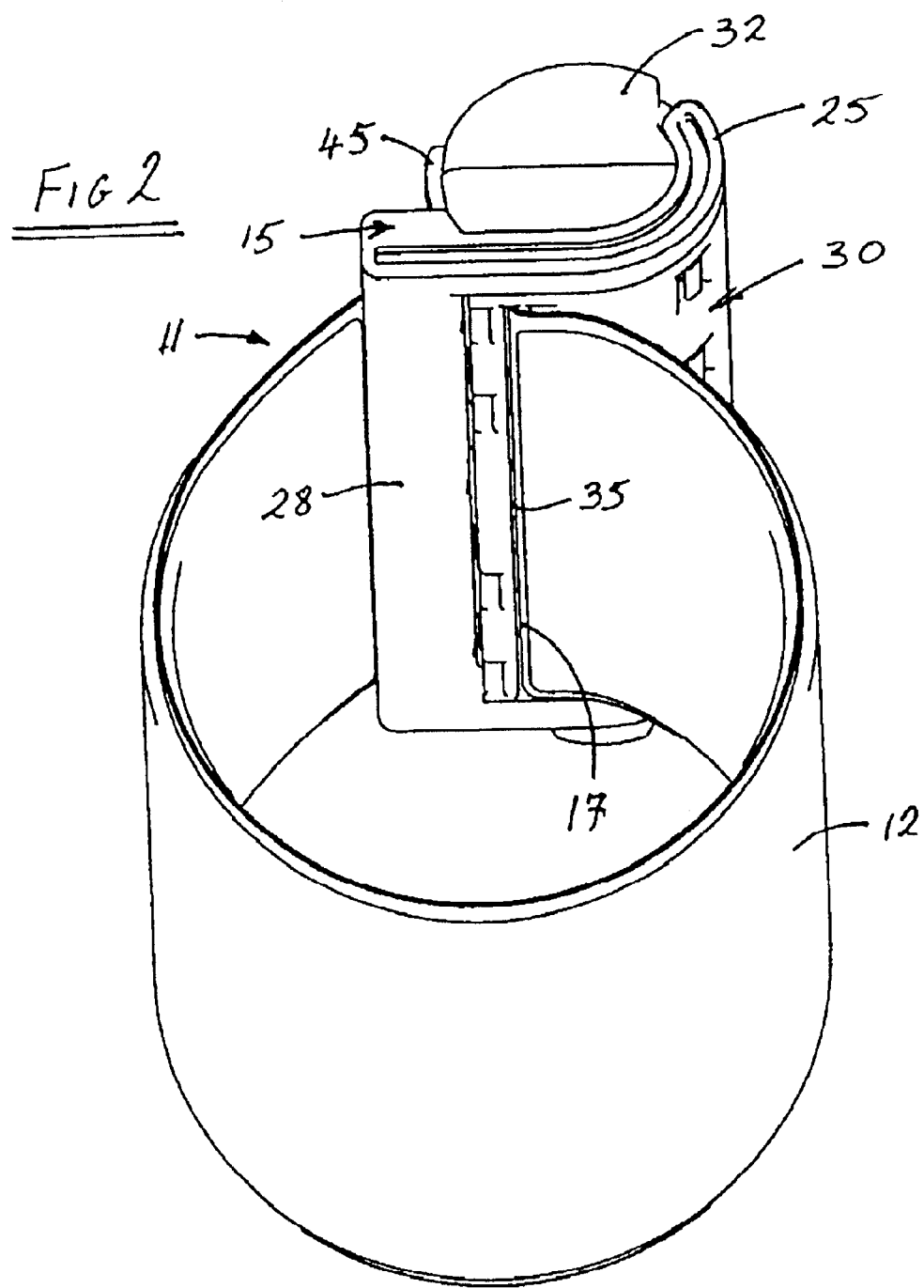
FIG. 2 is a schematic perspective view (from below and the opposite side) of the sphygmomanometer's cuff means shown in FIG. 1.

The sphygmomanometer 10 illustrated in FIG. 14 has cuff means 11 comprising a single inflatable compartment 12 in the form of an elongate bag or bladder of generally rectangular shape. One wall of the inflatable compartment 12 is provided with a pair of hollow spigots 14,16 for the passage of air into and/or out of the compartment 12. The hollow spigot 14 is connected via a rubber tube 18 and a one-way relief valve 20 to a compressible rubber inflating bulb 22. The hollow spigot 16 is connected via a rubber tube 24 to an appropriate pressure guage 26 (e.g. a mercury column guage or an aneroid or other pressure-measuring instrument).

The elongate rectangular inflatable compartment 12 is sealed along its edges, and the spigots 14,16 are located adjacent one shorter end or edge 13 of the compartment 12. That sealed end 13 is attached to an end unit 15 which comprises a pair of curved support arms 25 extending (in the same direction) from the opposite ends of a cross-piece 28. The face of the cross-piece 28 directed away from curved support arms 25 is provided with an L-section recess 27 in which a closure bar 29 fit's. The sealed end 13 of inflatable compartment 12 sits within the L-section recess 27, and the closure bar 29 serves to clamp this sealed end 13 in position to the end unit 15. To further enhance attachment of this compartment end 13 to end unit 15, a series of screws or like fasteners may extend (through holes 23) between the cross-piece 28 and the closure bar 29—and, optionally, also through the sealed end 13—to sandwich the compartment's sealed end 13 between parts 28 and 29.

Figure 3:
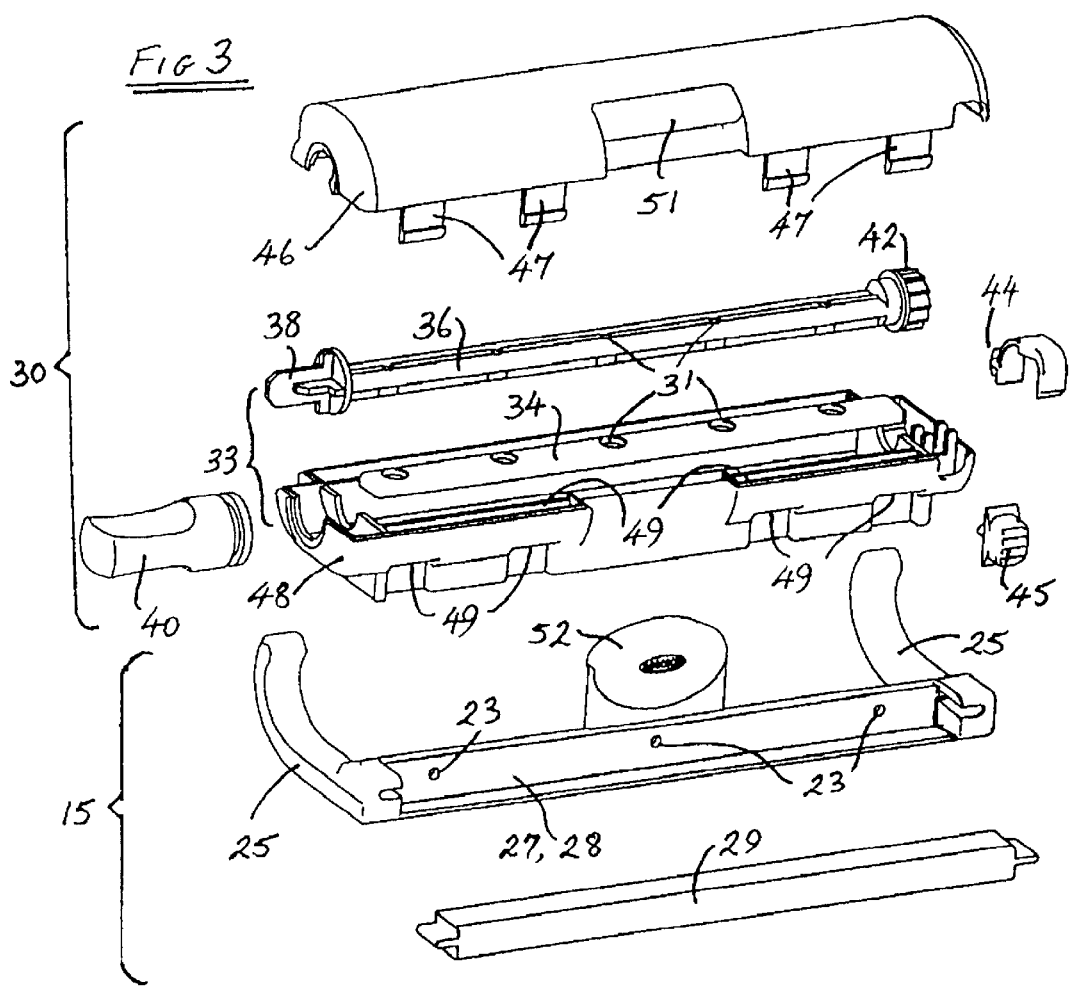
FIG. 3 is an exploded perspective view (from the front and said one side) of parts of the cuff means shown in FIG. 1.
Figure 4:
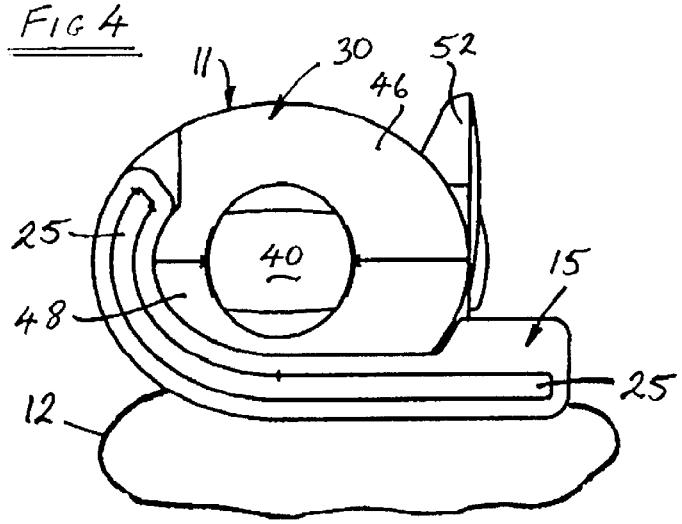
FIG. 4 is a schematic end view (from said one side) of the cuff means shown in FIG. 1.
Figure 8:
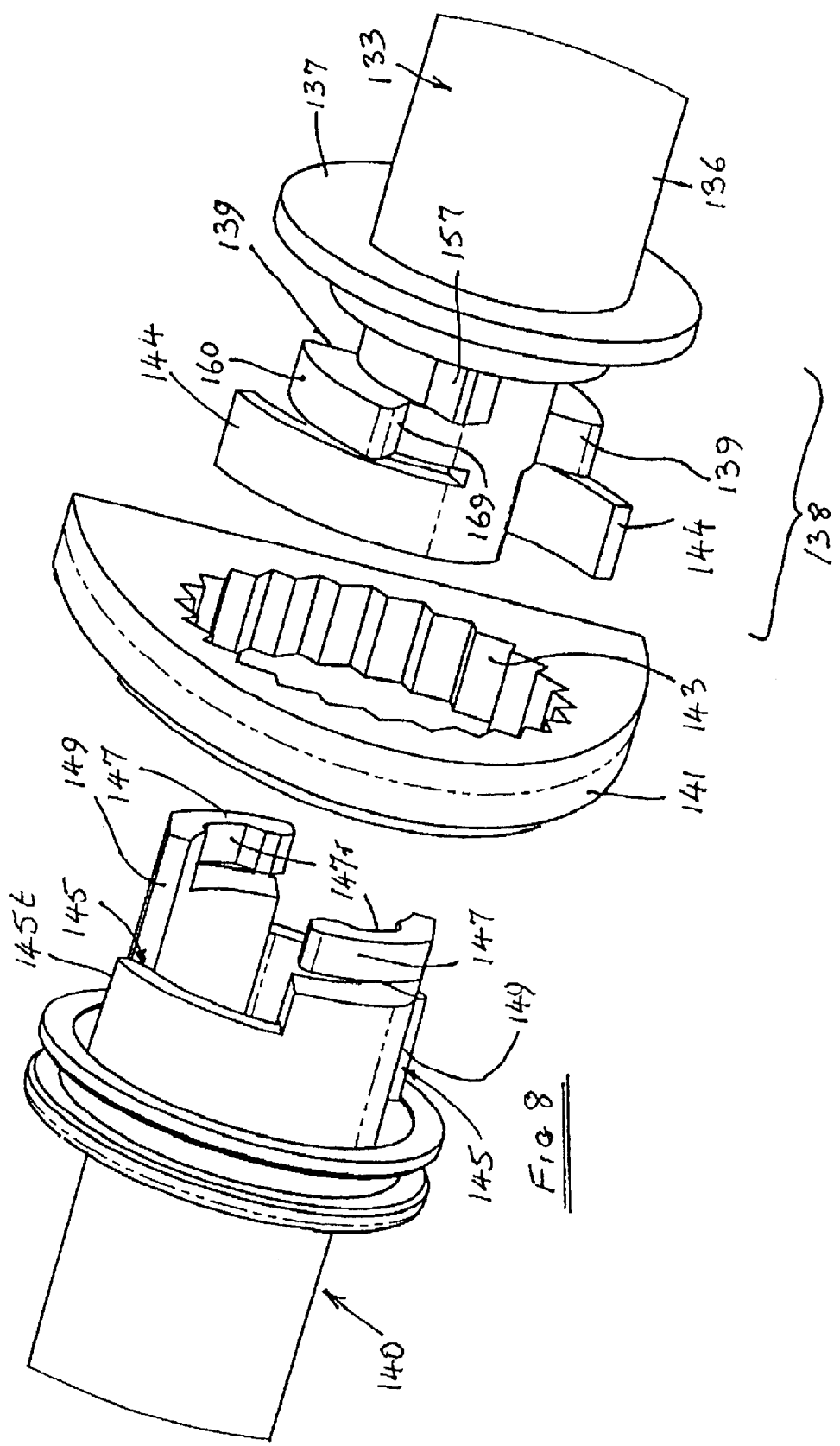
FIG. 8 is an exploded view of the ratchet device parts shown in FIG. 7.
Figure 9:
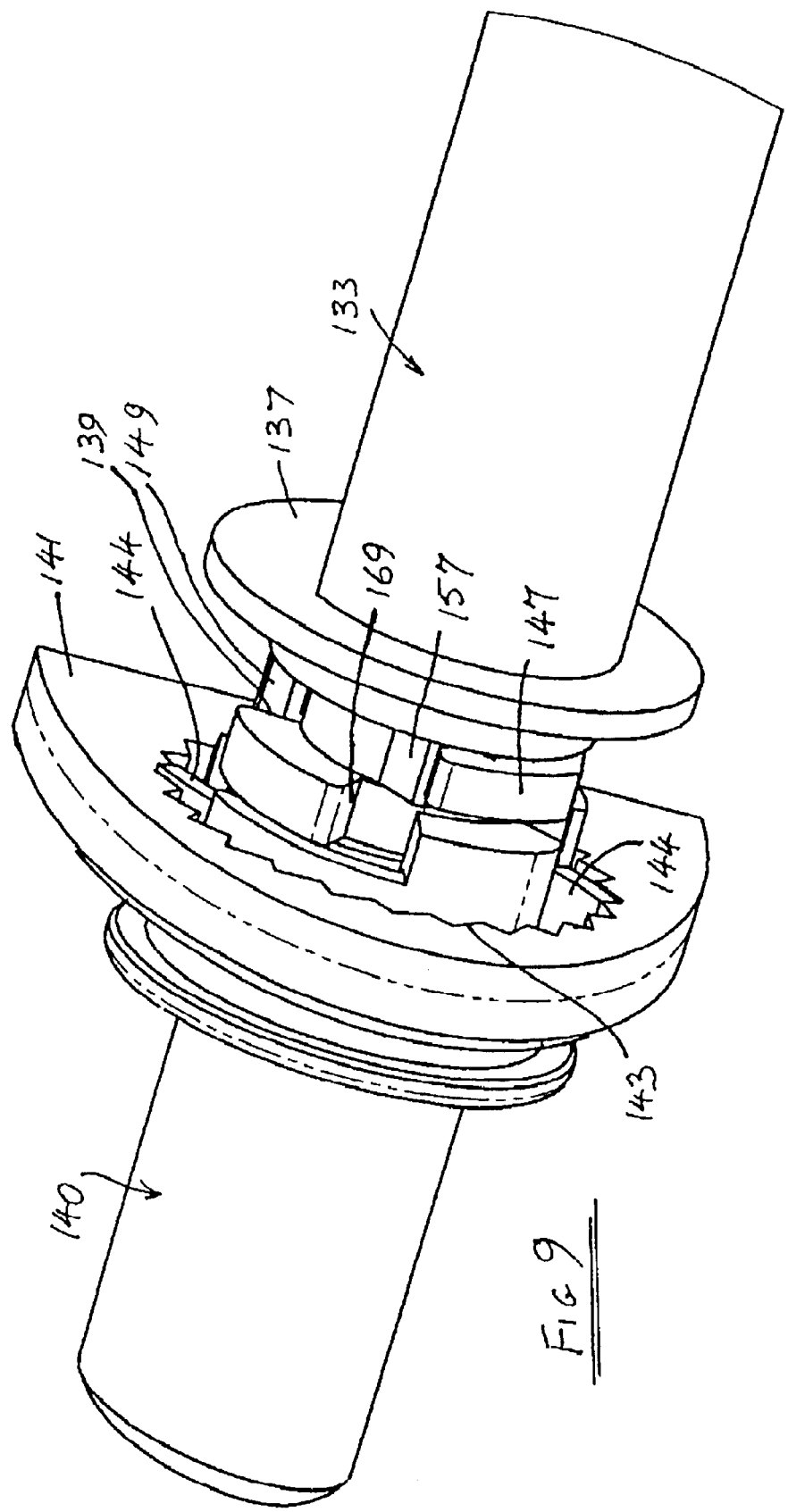
FIG. 9 is a perspective view of the ratchet device parts that are shown in FIG. 8 when they are interengaged.
Figure 10:
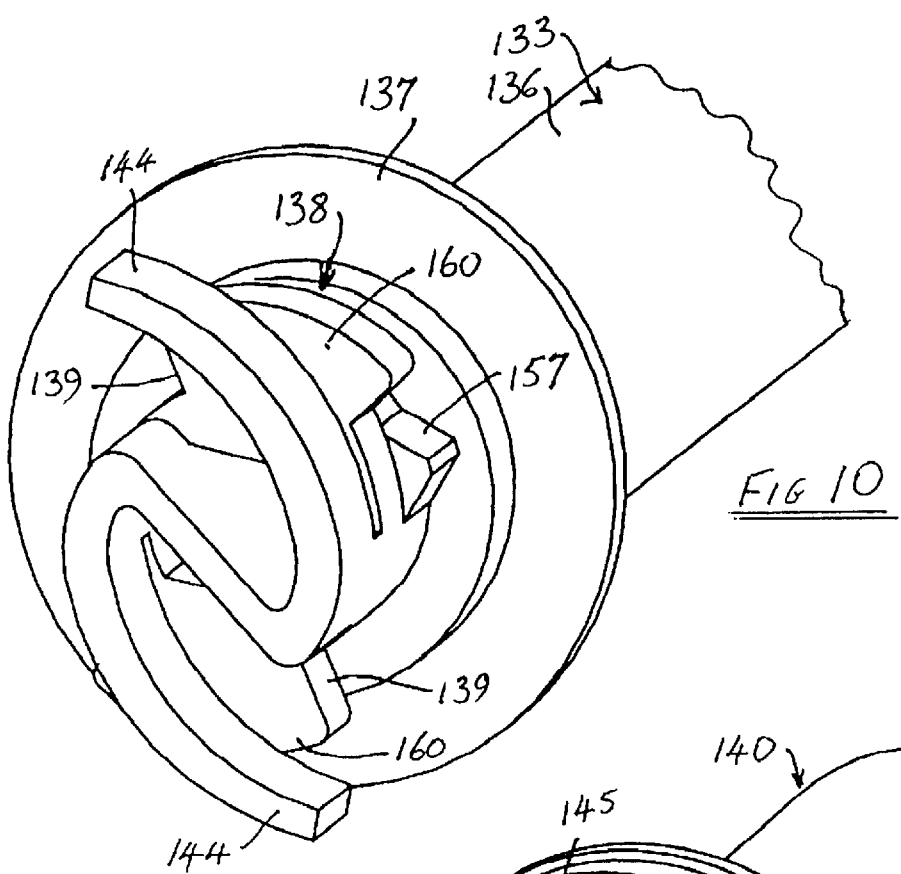
FIG. 10 is a perspective view of the end of a spindle part that is shown in FIGS. 6 to 9.
Figure 11:
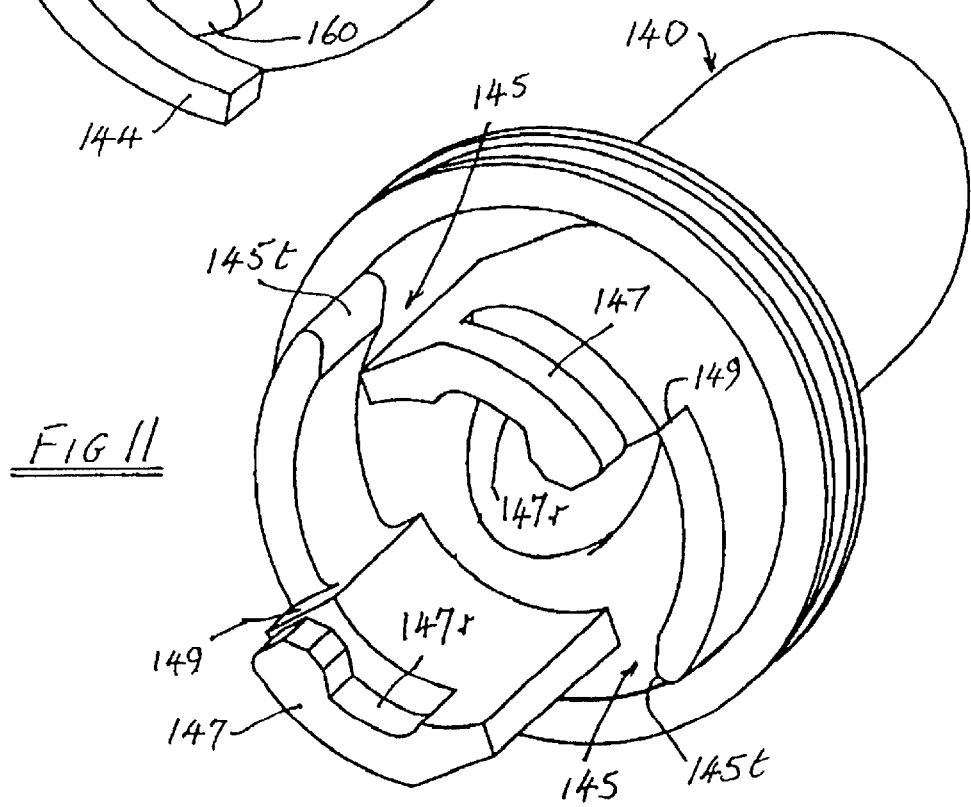
FIG. 11 is a perspective view of the end of a knob unit that is shown in FIGS. 6 to 9.

The opposite sealed end 17 of the rectangular inflatable compartment 12 is associated with a cuff constricting unit 30 that comprises a generally cylindrical elongate casing 32 having a slot 35 through which the elongate inflatable compartment 12 enters the casing. The latter houses and rotatably supports an internal spindle 33 (FIG. 3). The spindle 33 comprises a pair of inter-fitting elongate parts 34,36 between which the sealed end 17 of inflatable compartment 12 is sandwiched and clamped. To enhance this clamping attachment, a plurality of fasteners (e.g. screws) may extend (through holes 31) between the inter-fitting parts 34,36 and, optionally, also through the cuff's sealed end 17.

Part 36 of spindle 33 is provided at one end with an extension 38 of cruciform cross-section which fits within a correspondingly-shaped recess in a knob 40 that sits in an end wall of casing 32 to project outwardly of the casing. The opposite end of spindle part 36 is provided with a ratchet wheel 42, the casing 32 being internally provided with a pawl 44 that resiliently engages the ratchet wheel 42. A push button 45 mounted in the casing 32 to project laterally outwardly of the casing, is operable on the pawl 44 such that when the button 45 is depressed the pawl 44 is disengaged from the ratchet wheel 42. Advantageously the pawl 44 is molded of plastics material and is of a shape which renders it inherently resilient so that no separate spring is required to provide the resilient engagement force between it and the ratchet wheel 42.

To facilitate fitting and/or mounting of the parts 33–45 in the casing 32, the latter is formed as two parts 46,48 molded of plastics material such as to be capable of interconnecting with one another via undercut tabs 47 (on one part 46) that can extend through slots 49 (in the other part 47) and snap under the lower defining edges of those slots 49. The casing part 46 is also molded with a recess 51 which in use is to receive latchingly an undercut tab 52 that is molded integrally with cross-piece 28 of the end unit 15 (see FIG. 1).

In use, to measure a subject's blood pressure, the end unit 15 is located on the bicep, the inflatable bladder or bag that is defined by or is housed within the cuff 12 is wrapped or placed loosely around the subject's arm (usually the left arm) above elbow, and the constrictor unit 30 is placed into the cradle provided by the curved arms 25 of end unit 15 before being snap-connected to end unit 15 via snap fastener parts 51,52. The knob 40 is then rotated to wind up the cuff 12 about the spindle 33 and draw the cuff 12 into the housing 32 until the cuff—with units 15 and 30—provides a snug fit around the subject's upper arm. It will be appreciated that the arrangement allows the cuff element 12, on its own, to encompass at least 80% of the circumference of the upper arm of any subject (i.e. whatever size of upper arm the subject may have) and that the cuff 12 is in a position appropriate to shut off blood flow in the brachial artery when the bag (which the cuff 12 defines or contains) is inflated.

It will also be appreciated that the ratchet wheel 42 and its co-operating pawl 44 permit rotation of the spindle 33 in this "cuff-winding-in" direction and, as long as the button 45 is not depressed, prevent spindle rotation in the contra-direction which would allow loosening of the cuff 12 from conforming engagement of and around the subject's upper arm.

Using bulb 22, air is pumped into the bag 12 via the one-way valve 20, tube 18 and spigot 14, the effective volume of the bag being only that which conforms to the perimeter of the subject's upper arm, i.e. which is external of the constriction provided by the constrictor unit 30. This is because the ratchet mechanism 42–45 prevents any air-pressure-induced unwinding of the cuff from off the spindle 33 and thus prevents any increase in the inflatable length of the cuff beyond that to which it was initially set when the cuff was initially wound into the casing 32. The pumped air supply is continued until the subject's pulse in the brachial artery in the upper arm disappears. The reading of the guage 26 at this moment gives the systolic blood pressure, i.e. the pressure necessary to suppress the maximum pressure of blood in the artery. The air pressure within the bladder is then allowed to decrease slowly via the one-way relief valve 20 whilst the (expected) pulse beat is monitored by the user's stethoscope. As the air pressure compressing the artery is diminished, the pressure reading on gauge 26 at which the maximum pulse wave is (again) obtained marks the diastolic pressure, i.e. provides a measure of the pressure when the heart is in diastole with arterial pressure at its minimum.

After the subject's blood pressure has been measured, the release button 45 can be depressed to disengage pawl 44 from ratchet wheel 42 so as to permit loosening of the cuff 12 from around the subject's arm by counter-rotating the wind-up knob 40 and/or by simply pulling the cuff 12 outwards from the casing 32. Once the cuff is loose, the subject or the person (e.g. nurse or doctor) responsible for obtaining the subject's blood pressure can, using a thumb or their fingers, disengage the two units 15 and 30 from one another by separating the inter-latched parts 51 and 52.

It will be appreciated that the fasteners provided to attach either or each end 13,17 of the cuff 12 to its associated unit 15,30 may be other than screws. For example they may comprise spigots provided with undercut tips to snap fit into the holes 23 and/or 31.

The embodiment of FIGS. 5 to 11 functions in substantially the same manner as that of FIGS. 1 to 4 and structurally similar parts are in general identified by the same reference numeral with the addition of 100.

The sphygmomanometer 110 of FIGS. 5 to 11 has an end unit 115 that fits into an elongate recess 127 in the outer surface of the generally cylindrical, elongate casing 132 of cuff constrictive unit 130. The end unit 115 comprises two mutually co-operating elongate parts 128,129 (FIG. 6) that together form a main body or cross-piece. The sealed end 13 of the inflatable compartment 12 is sandwiched between the parts 128,129 and secured to them with screw fastenings through holes 123.

The two parts 128,129 of end unit 115 also clamp between them a clip 150 of generally J-shaped form having a short tab-like limb 125 and a longer detent-like limb 152. The tab-like limb 125 can enter a recess 125r in the wall of casing 132, and the detent-like limb 152 has a rib 151 that can co-operate with the edge of a cavity 153 provided in the outer surface of the wall of casing 132. This clip 150 provides a very reliable detent device for fastening the end unit 115 to the casing 132, yet permits their separation by appropriate lifting of limb 152.

The clip's bight wall 154 (FIG. 6) is provided with a central bead 155 or like line of greater thickness and with a decreasing wall thickness approaching the bight wall's side edges. In addition, the opposed edges 158a, 158b and 159a, 159b of the recess in parts 128,129 of end unit 115 that accommodates the clip, are provided as oppositely directed, mutually divergent surfaces having a form substantially that of the symbols >< in elision. This oppositely angled arrangement of the side surfaces of the clip's bight wall 154 and of the opposed edges 158a,158b and 159a,159b of the clip accomodating recess, allows the clip's bight wall 154 to be pivotable in each direction about its bead 155 (that is located between the divergent walls 158a, 159a and 158a, 159b).

It is this co-operation between clip 150 and casing 132 that permits a measure of twisting angular movement, e.g. of the order of between 5° and 15°, between the end unit 115 and the casing 132 without those parts becoming separated from one another. This measure of twisting angular movement permits the looped portion of inflatable compartment 12 (that extends from end unit 115 to the slot 135 in the wall of casing 132) to accommodate the tapering nature of the patient's upper arm—and can do this whether the arm thickness decreases or (in some patients) increases as the arm extends towards the patient's hand, and whether the inflatable cuff is placed on the left arm (as is usual) or (for some patients) is placed on the right arm.

As the elongate rectangular cuff or compartment 12 extends through slot 135 of casing 132 it follows a path whereby it bends back or reverses upon itself—i.e. it approaches the slot from the same left or right side both internally and externally of the casing 132. This tends to provide mutually opposing inflation forces to each of the internal casing surface and the external casing surface adjacent the slot 135 such as to aid in the constrictive effect and in minimising any tendency for the inflation forces internally of the casing to separate the two co-operating casing parts 146,148.

The casing 132 houses and rotatably supports an internal spindle 133 comprising a pair of inter-fitting elongate parts 134,136. The sealed end 17 of the cuff or compartment 12 is sandwiched and clamped between two parts 134,136 and, to enhance this clamping attachment, a plurality of screws or other fasteners may extend through holes 131 provided in the inter-fitting parts 134,136 (and, optionally, also through the cuff's sealed end 17). Part 136 of spindle 133 is provided with both of the spindle's end discs 137 and is also provided with an axially outward extension 138 that is to co-operate with a knob unit 140 projecting through an apertured end wall 141 of the casing 132. This apertured end wall 141 is provided as a separate element (e.g. of a more rigid plastics material to that employed for the casing parts 146,148) that is retained firmly in position by the casing's main co-operating parts 146,148. The casing end wall 141 has its aperture formed as a ring of saw-like ratchet teeth 143, i.e. having sequential steep-rake and shallow rake surfaces.

As best shown in FIGS. 7 to 11, the spindle's extension 138 is molded integrally with a pair of diametrically opposite, spirally directed, resilient pawl limbs 144 of which the free ends are to engage and co-operate with the saw-like ratchet teeth 143. The spindle's extension 138 is also molded integrally with a pair of diametrically opposite lobes 160 defining a first pair of diametrically aligned radial shoulders 169 and, angularly spaced therefrom, a second pair of diametrically aligned radial shoulders 139. The radial shoulders 139 are in use engageable by a pair of diametrically opposite radial flanges 149 molded integrally on knob unit 140. The knob unit 140 is also provided with a pair of diametrically opposite slots 145 through which the resilient limbs 144 extend.

To tighten the external loop of the cuff or compartment 12 about the upper arm of a patient, the knob unit 140 is rotated clockwise. This clockwise rotation of knob unit 140 will cause its flanges 149 to abut against steps 139 of the spindle extension 138 and cause spindle 133 to rotate clockwise to wind in excess lengths of compartment 12. Such clockwise rotation of the spindle 133 is unimpeded since the resilient pawl limbs 144 slip past and over the shallow rake surfaces of the saw-like teeth 143 in the end wall 141. The limbs 144 may possibly also be slightly deflected radially inwardly (towards the spindle's axis) as they ratchet past the saw-like internal teeth 143.

In contrast, any tendency to anti-clockwise rotation of spindle 133 due to tension in the inflatable compartment or cuff 12 will be prevented by engagement between the end tips of the pawl limbs 144 and the steeply raked surfaces of the saw-like teeth 143.

However, when it is desired to effect loosening of the external loop of inflatable compartment or cuff 12 from off the patient's arm, the knob unit 140 is rotated anti-clockwise. As soon as such anti-clockwise rotation is initiated, the (now leading) trailing edge 145t of each slot 145 engages the outer surface of the spirally directed resilient pawl limb 144 that projects through that slot, and deflects it inwardly towards the common axis of the knob and spindle. This action moves the free ends or tips of the limbs 144 out of their engagement of the saw-teeth 143 and removes the restraint to the anti-clockwise rotation of spindle 133 and to compartment 12 being unwound from it.

To ensure that any further anti-clockwise rotation of knob unit 140 does not cause damage to the parts and/or does not move co-operating parts to positions in which their subsequent co-operation (upon clockwise rotation of the knob unit) would be prejudiced, the spindle extension 138 and the knob unit 140 may be provided with co-operating detent means 147,157. As illustrated, the co-operating detent means on knob unit 140 comprises a pair of diametrically opposite, generally arcuate, resilient limbs 147 molded integrally at the free end of knob unit 140, each limb 147 having an undercut recess 147r in its radially inward surface. The co-operating part on spindle extension 138 is provided by a pair of diametrically opposite, triangular lobes 157 that can snap into the undercut recess 147r in each limb 147 as the knob unit 140 is rotated anti-clockwise past the leading end of each arcuate resilient limb 147 (which is deflected resiliently outwardly to permit this motion).

It will be appreciated that the above-described parts 138 to 157 provide a one-hand operable ratchet mechanism having a rotatable input member (knob unit 140) and a rotatable output member (spindle 133), rotation of the input member in a first direction effecting rotation of the output member in that direction but preventing rotation of the output member in a second, opposite direction, and rotation of the input member in the opposite second direction permitting rotation of the output member in that second direction. It will be noted that the illustrated embodiment achieves this by providing first and second mutually engageable ratchet means that, when the input member is rotated in said first direction are in mutual co-operative engagement to prevent said rotation of the output member in the second direction and that are disengaged when the input member is rotated in the said opposite, second direction—to permit said rotation of the output member in the second direction.

It will be apparent from the foregoing description of the embodiment of FIGS. 5 to 11 that, after the subject's blood pressure has been measured, and the pressure in the cuff 12 released, the cuff means can be released from off the subject's arm in one and/or other of two ways. One way is by disengaging the ratchet mechanism's co-operatively engageable parts 143,144 to permit withdrawal of a wound-up cuff portion from the housing 132, the thus-extended length of cuff externally of the housing being then freely movable with respect to the subject's arm and allowing the apparatus to be slipped off the subject's arm. The second way is by simply uncoupling the resilient clip 150 from off the casing 132 to free the apparatus as a whole from off the subject's arm.

It will be appreciated that the embodiment of FIGS. 5 to 11 can be modified in a number of ways.

In one modification, the end wall 141 is not a separate component but, instead, is molded integrally with one or other of the two mutually co-operating parts 146,148 of casing 132.

In another modification, illustrated as the embodiment of FIGS. 12 to 14, the cooperating detent means 147,157 of the embodiment of FIGS. 5–11 are omitted and, instead, the angular extent of each slot 145 in knob unit 140 and of each lobe 160 on spindle end 138 is altered. Each slot 145 is widened to permit the pawl arm 144 normally projecting therethrough to be deflected wholly inwardly of slot 145 as the (now leading) trailing edge 145t engages that arm 144 upon anti-clockwise rotation of knob 140. Thus the arms 144 do not impede anti-clockwise rotation of the knob 140. In addition, the angular extent of each lobe 160 on the spindle end extension 138 is reduced to provide a pair of diametrically opposite radial shoulders 169 angularly spaced from the shoulders 139. The arrangement is such that, upon anti-clockwise rotation of knob 140, the shoulder 169 of each lobe 160 is engaged by an associated radial flange or surface 168 provided by the knob 140 unit. This arrangement ensures that anti-clockwise rotation of knob unit 140 can release ratchet co-operation between parts 134,144 but not move so far anti-clockwise that the inherent co-operative relationship between the parts is disturbed to an extent preventing their subsequent cooperation upon later clockwise rotation of the knob unit 140 for re-use of the cuff means. In other words, after initial anti-clockwise rotation of the knob unit 140 with respect to the spindle 133, further anti-clockwise rotation of the knob unit 140 is accompamied by corresponding anti-clockwise rotation of the spindle to unwind the cuff 12 therefrom.

Optionally, the knob unit 140 of FIG. 14 is (or, indeed, that of FIG. 11) may be provided with a pair of diametrically opposite arcuate limbs 170 which, when the knob unit 140 is rotated clockwise, engage root-adjacent portions of the pawl members 144 and urge the pawl members 144 outwardly through the slots 145. These limbs 170 thus aid the inherent resiliency of the pawl members 144 and ensure that they engage the ratchet teeth 143 during such clockwise rotation of the knob unit 140.

Figure 15:
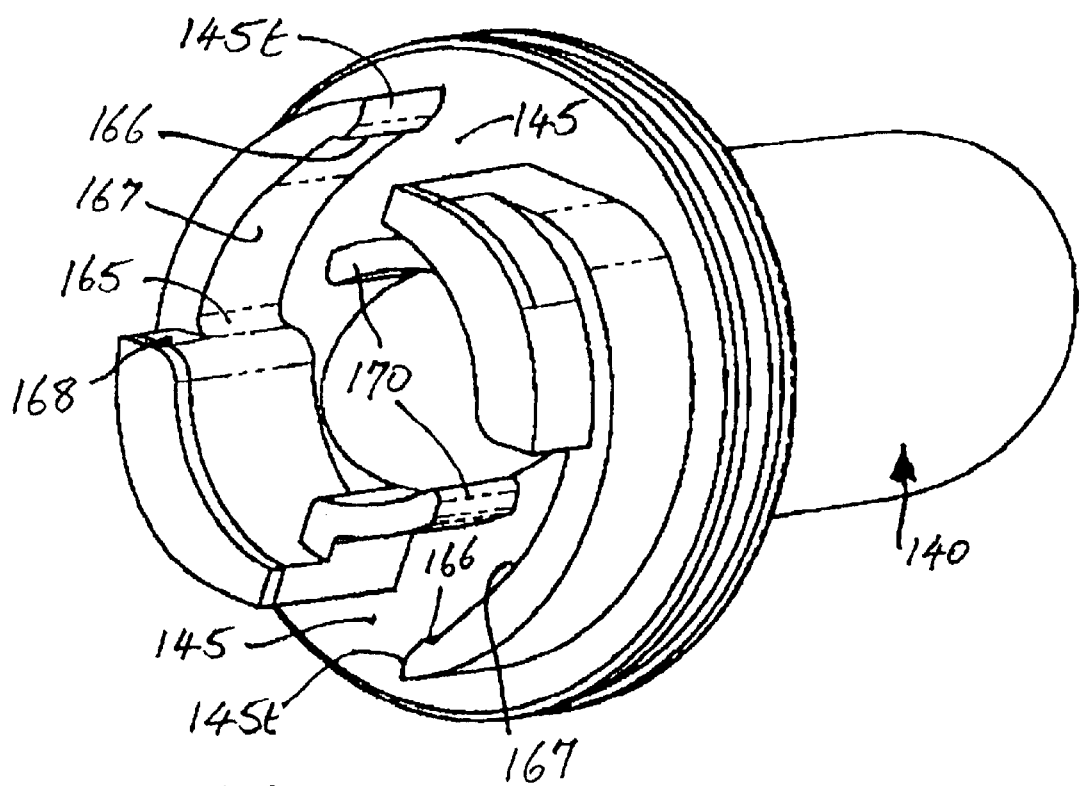
FIG. 15 is a view similar to that of FIG. 11 and FIG. 14 but of a further modification of the knob unit.

In a still further modification illustrated in FIG. 15, parts 147 and 157 are again omitted but the latching co-operation between them is replaced by providing the knob unit 140 with an elongate arcuate recess 167 in the interior face of the wall defining the edge 145t of the slot 145. The ends of this elongate arcuate recess 167 are defined at one end by a generally radially directed bounding surface 166 adjacent slot 145 and at the other end by a somewhat curved surface 165, the distance between surfaces 165 and 166 being sufficient to accomodate a pawl 144. When the knob unit 140 of FIG. 15 is rotated anti-clockwise to disenage (i.e. release) the ratchet mechanism between pawl 144 on spindle 133 (of either FIG. 10 or FIG. 13) and ratchet teeth 143, the pawl 144 slides relatively past the wall's edge 145t and, due to its inherent resiliency, enters somewhat fittingly into the recess 167 to engage behind the bounding surface 166 of the recess. Thus, here again, after initial anti-clockwise rotation of the knob unit 140 with respect to the spindle 133, further anti-clockwise rotation of the knob unit 140 is accompanied by corresponding anti-clockwise rotation of the spindle to unwind the cuff 12 therefrom.

It will be appreciated that in use of the embodiments of the sphygmomanometer illustrated in FIGS. 5 to 15 to measure a subject's blood pressure, the end unit 115 is snap-connected to the constrictor unit 130 to form the inflatable bladder or bag as a loop that encompasses the subject's arm (usually the left arm) above elbow. The knob unit 140 is then rotated to wind up the cuff 12 about the spindle 133 and draw the cuff 12 into the housing 132 until the cuff—with units 115 and 130—provides a snug fit around the subject's upper arm. It will be appreciated that the arrangement allows the cuff element 12, on its own, to encompass at least 80% of the circumference of the upper arm of any subject (i.e. whatever size of upper arm the subject may have) and that the cuff 12 is in a position appropriate to shut off blood flow in the brachial artery when the bag (which the cuff 12 defines or contains) is inflated.

It will also be appreciated that the above-described ratchet mechanism permits rotation of the spindle 133 in this "cuff-winding-in" direction and, as long as it is not subject to counter-rotation, prevents spindle rotation in the contra-direction which would allow loosening of the cuff 12 from conforming engagement of and around the subject's upper arm.

Using the inflation bulb, air is pumped into the bag 12 via the one-way valve 20 and its associated tube and spigot, the effective volume of the bag being only that which conforms to the perimeter of the subject's upper arm, i.e. which is external of the constriction provided by the constrictor unit 130. This is because the ratchet mechanism prevents any air-pressure-induced unwinding of the cuff from off the spindle 133 and thus prevents any increase in the inflatable length of the cuff beyond that to which it was initially set when the cuff was initially wound into the casing 132. The pumped air supply is continued until the subject's pulse in the brachial artery in the upper arm disappears. The reading of the guage at this moment gives the systolic blood pressure, i.e. the pressure necessary to suppress the maximum pressure of blood in the artery. The air pressure within the bladder is then allowed to decrease slowly via the one-way relief valve whilst the (expected) pulse beat is monitored by the user's stethoscope. As the air pressure compressing the artery is diminished, the pressure reading on the gauge at which the maximum pulse wave is (again) obtained marks the diastolic pressure, i.e. provides a measure of the pressure when the heart is in diastole with arterial pressure at its minimum.

After the subject's blood pressure has been measured, the knob unit 45 can be rotated in the opposite direction so as to permit loosening of the cuff 12 from around the subject's arm. Such counter-rotation pushes additional length of cuff outwards of the casing 132 and/or simply enables pulling of the cuff 12 outwards from the casing 132. Once the cuff is loose, the subject or the person (e.g. nurse or doctor) responsible for obtaining the subject's blood pressure can, using a thumb or their fingers, disengage the two units 115 and 130 from one another by separating the inter-latched parts 151 and 152.

Other modifications and embodiments of the invention, which will be readily apparent to those skilled in this art, are to be deemed within the ambit and scope of the invention, and the particular embodiment(s) hereinbefore described may be varied in construction and detail, e.g. interchanging (where appropriate or desired) different features of each, without departing from the scope of the patent monopoly hereby sought. For example the guage 26 may be a simple mercury manometer, or may be an aneroid instrument, or may be an electronic pressure measuring instrument. Also for example, and either additionally or alternatively, the fasteners provided to attach either or each end 13,17 of the cuff 12 to its associated unit 15,30 or 115,130 may be other than screws. For example they may comprise spigots provided with undercut tips to snap fit into the holes 23,123 and/or 31,131.

What is claimed is:

1. A cuff member for a sphygmomanometer comprising a housing, a spindle manually rotatable therein, and an inflatable cuff having one end attached to said spindle and being wound spirally on said spindle, the spiral-wound portion of the cuff in use remaining at least partially inflatable but providing the effect of a constriction at a position along its length dependent on the extent of the spiral wound portion, a length susceptible to inflation, the inflatable cuff extending through an opening in the housing, an end unit attached to the other end of the inflatable cuff, a releasable fastening member for releasably fastening said end unit to the housing when a desired effective length of cuff has been withdrawn from the housing via said opening to extend in a loop around the upper arm of a patient, and a ratchet mechanism mounted in cooperation with the spindle to allow withdrawal of the cuff from the housing when the spindle is manually rotated in one direction and restrain withdrawal of the cuff from the housing for rotation of the spindle in the opposite direction.

2. Cuff member according to claim 1, characterized by the cuff, in use, adopting a frusto-conical form to accommodate the taper of a subject's limb.

3. Cuff member according to claim 1 characterized in that the opening is provided by a slot formed between two cooperating parts of the housing.

4. Cuff member according to claim 1, characterized in that the releasable fastening member comprises mutually co-operable snap-fastening attachments provided on respectively the end unit and the housing.

5. Cuff member according to claim 1, characterized in that the releasable fastening member is attached to one of the end unit and the housing in a manner permitting relative twisting between said end unit and said housing.

6. Cuff member according to claim 5, wherein the degree of permitted twisting is in the range 5° to 15°.

7. Cuff member according to claim 6, wherein the releasable fastening member is attached to one of the end unit and the housing in a manner permitting their relative twisting such that the taper of a subject's limb is automatically accommodated in use by the permitted relative twisting permitted by said releasable fastening.

8. Cuff member according to claim 1, characterized by said ratchet mechanism being one-hand operable and comprises a rotatable input member and a rotatable output member, rotation of the input member in a first direction effecting rotation of the output member in that direction but preventing rotation of the output member in a second, opposite direction, and rotation of the input member in the opposite second direction permitting rotation of the output member in that second direction.

9. Cuff member according to claim 8, characterized in that said rotatable input member is a knob unit and the rotatable output member is constituted by said spindle, the knob and spindle being coaxial with one another.

10. Cuff member according to claim 8, characterized by first and second mutually engageable ratchets that, when the input member is rotated manually in said first direction, are in mutual co-operative engagement to prevent said rotation of the output member in the second direction, and that are disengaged when the input member is rotated manually in the said opposite, second direction to enable said rotation of the output member in the second direction by the same one-handed operation.

11. A cuff member for a sphygmomanometer comprising a housing having a wall provided with an elongate opening, a spindle rotatable therein, and a cuff inflatable throughout its length, wherein the inflatable cuff extends through said opening, has one end attached to said spindle and is wound spirally on said spindle, the spiral-wound portion of the cuff in use remaining at least partially inflatable but restrained against expansion at a position along said length dependent on the extent of the spiral wound portion, whereby the said length can be manually varied from a maximum to an effective length extending away from the spindle and less than the maximum further characterized by a one hand operable ratchet mechanism to restrain withdrawal of the cuff from the housing, and a release operable to permit such withdrawal, said ratchet mechanism comprising a rotatable input member including a knob unit and a rotatable output member co-axial with the knob and constituted by said spindle, rotation of the input member in a first direction effecting rotation of the output member in that direction but preventing rotation of the output member in a second, opposite direction, and rotation of the input member in the opposite second direction permitting rotation of the output memeber in that second direction.

* * * * *